US011376327B2

(12) United States Patent
Nguyen et al.

(10) Patent No.: US 11,376,327 B2
(45) Date of Patent: *Jul. 5, 2022

(54) STABLE TRANSDERMAL AMPHETAMINE COMPOSITIONS AND METHODS OF MANUFACTURE

(71) Applicant: Noven Pharmaceuticals, Inc., Miami, FL (US)

(72) Inventors: Viet Nguyen, Miami, FL (US); Jun Liao, Miami, FL (US); Prashant Patel, Miami, MD (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/827,190

(22) Filed: Nov. 30, 2017

(65) Prior Publication Data
US 2018/0207280 A1 Jul. 26, 2018

Related U.S. Application Data

(63) Continuation of application No. 14/208,367, filed on Mar. 13, 2014, now abandoned.

(60) Provisional application No. 61/790,077, filed on Mar. 15, 2013.

(51) Int. Cl.
| | |
|---|---|
| *A61K 47/32* | (2006.01) |
| *A61K 31/137* | (2006.01) |
| *A61K 9/00* | (2006.01) |
| *A61K 9/70* | (2006.01) |
| *A61L 31/12* | (2006.01) |

(52) U.S. Cl.
CPC ............ *A61K 47/32* (2013.01); *A61K 9/0014* (2013.01); *A61K 9/7007* (2013.01); *A61K 31/137* (2013.01); *A61L 31/129* (2013.01); *A61K 9/7053* (2013.01); *A61K 9/7061* (2013.01)

(58) Field of Classification Search
CPC .... A61K 47/32; A61K 9/0014; A61K 9/7007; A61K 31/137; A61L 31/129
See application file for complete search history.

(56) References Cited

U.S. PATENT DOCUMENTS

| | | | |
|---|---|---|---|
| 5,234,957 | A | 8/1993 | Mantelle |
| 5,332,576 | A | 7/1994 | Mantelle |
| 5,446,070 | A | 8/1995 | Mantelle |
| 5,719,197 | A | 2/1998 | Kanios et al. |
| 5,958,446 | A | 9/1999 | Miranda et al. |
| 6,024,974 | A | 2/2000 | Li |
| 6,024,976 | A | 2/2000 | Miranda et al. |
| 6,210,705 | B1 | 4/2001 | Mantelle et al. |
| 6,235,306 | B1 | 5/2001 | Miranda et al. |
| 6,316,022 | B1 | 11/2001 | Mantelle et al. |
| 6,348,211 | B1 | 2/2002 | Mantelle et al. |
| 7,846,916 | B2 | 12/2010 | Houze |
| 7,867,986 | B2 | 1/2011 | Houze |
| 7,879,831 | B2 | 2/2011 | Houze |
| 7,989,496 | B2 | 8/2011 | Hartwig et al. |
| 7,993,671 | B2 | 8/2011 | Mantelle et al. |
| 8,153,151 | B2 | 4/2012 | Houze |
| 8,187,628 | B2 | 5/2012 | Houze et al. |
| 8,216,606 | B2 | 7/2012 | Houze et al. |
| 8,231,906 | B2 | 7/2012 | Mantelle |
| 8,246,976 | B2 | 8/2012 | Nguyen |
| 8,277,838 | B2 | 10/2012 | Nguyen |
| 8,337,884 | B2 | 12/2012 | Mantelle et al. |
| 8,343,538 | B2 | 1/2013 | Kanios et al. |
| 8,632,802 | B2 | 1/2014 | Kanios |
| 8,703,175 | B2 | 4/2014 | Kanios et al. |
| 8,715,723 | B2 | 5/2014 | Kanios et al. |
| 8,784,874 | B2 | 7/2014 | Strauss |
| 8,784,877 | B2 | 7/2014 | Houze et al. |
| 8,852,628 | B1 | 10/2014 | Houze et al. |
| 8,865,207 | B2 | 10/2014 | Kanios et al. |
| 8,916,191 | B2 | 12/2014 | Kanios |
| 9,034,370 | B2 | 5/2015 | Kanios |
| 9,295,726 | B2 | 3/2016 | Kulakofsky et al. |
| 9,320,742 | B2 | 4/2016 | Mantelle |
| 9,456,993 | B2 | 10/2016 | Lambert |
| 9,474,722 | B2 | 10/2016 | Lambert |
| 9,717,697 | B2 | 8/2017 | Liao et al. |
| 9,730,900 | B2 | 8/2017 | Mantelle |
| 9,901,552 | B2 | 2/2018 | Lambert |
| 2003/0104041 | A1 | 6/2003 | Hsu |
| 2003/0170195 | A1* | 9/2003 | Houze ................. A61K 8/0208 424/70.16 |
| 2005/0169977 | A1 | 8/2005 | Kanios et al. |

(Continued)

OTHER PUBLICATIONS

Henkel, Druo-Tak and Gelva Transdermal Pressure Sensitive Adhesives, Sep. 2013. (Year: 2013).*
U.S. Appl. No. 15/877,925, filed Jan. 23, 2018, Robert L. Lambert.
International Search Report dated May 27, 2014 in application No. PCT/US2014/025627.
Office Action dated Mar. 24, 2016 in U.S. Appl. No. 14/208,367 (US 2014-0322298).
Office Action dated Sep. 11, 2015 in U.S. Appl. No. 14/208,367 (US 2014-0322298).

*Primary Examiner* — Genevieve S Alley
(74) *Attorney, Agent, or Firm* — Foley & Lardner LLP

(57) ABSTRACT

Described are transdermal drug delivery compositions comprising amphetamine, methods of making transdermal drug delivery compositions comprising amphetamine, and therapeutic methods of using them. In specific embodiments, the compositions are free of components with moieties that are reactive with amphetamine. In specific embodiments, the compositions are manufactured using solvents free of components with moieties that are reactive with amphetamine. Therapeutic methods using the compositions also are described.

14 Claims, No Drawings

(56) References Cited

U.S. PATENT DOCUMENTS

| | | | |
|---|---|---|---|
| 2007/0212410 A1* | 9/2007 | Kanios | A61K 31/46 424/457 |
| 2009/0215808 A1* | 8/2009 | Yum | A61K 31/4458 514/282 |
| 2011/0165222 A1* | 7/2011 | Mantelle | A61L 15/44 424/448 |
| 2014/0182597 A1 | 7/2014 | Patel et al. | |
| 2014/0188056 A1 | 7/2014 | Mori et al. | |
| 2014/0243764 A1 | 8/2014 | Kanios et al. | |
| 2014/0271792 A1 | 9/2014 | Liao | |
| 2014/0271865 A1* | 9/2014 | Lambert | A61K 31/137 424/487 |
| 2014/0276478 A1 | 9/2014 | Liao et al. | |
| 2014/0276479 A1 | 9/2014 | Nguyen et al. | |
| 2014/0276483 A1 | 9/2014 | Liao et al. | |
| 2014/0322298 A1 | 10/2014 | Nguyen et al. | |
| 2015/0104495 A1 | 4/2015 | Nguyen et al. | |
| 2015/0342899 A1 | 12/2015 | Kulakofsky et al. | |

* cited by examiner

STABLE TRANSDERMAL AMPHETAMINE COMPOSITIONS AND METHODS OF MANUFACTURE

CROSS-REFERENCE TO RELATED APPLICATIONS

This application is a continuation of U.S. patent application Ser. No. 14/208,367, filed Mar. 13, 2014, which claims the benefit under 35 U.S.C. § 119(e) to U.S. provisional application 61/790,077, filed Mar. 15, 2013, the contents of each of which are incorporated here by reference in their entirety.

BACKGROUND

The present invention relates generally to the transdermal delivery of amphetamine, transdermal drug delivery compositions comprising amphetamine, methods of manufacturing transdermal drug delivery compositions comprising amphetamine, and therapeutic methods using transdermal drug delivery compositions comprising amphetamine. Transdermal drug delivery compositions comprising amphetamine are useful for transdermally delivering amphetamine, such as may be desired for achieving central nervous system stimulation, for the treatment of attention deficit disorder (ADD) and/or Attention Deficit/Hyperactivity Disorder (ADHD), and/or for the treatment of narcolepsy.

Many factors influence the design, manufacture, and performance of transdermal drug delivery compositions. These include the individual drugs themselves, the physical and chemical characteristics of the compositions' components and their performance and behavior relative to other components, external and environmental conditions during manufacturing and storage, properties of the application site, the desired rate of drug delivery and therapeutic onset, the desired drug delivery profile, and the intended duration of delivery, among others.

Compositions for the transdermal delivery of amphetamine are known, but there remains a need for compositions that are stable against the formation of amphetamine reaction products and degradation products.

SUMMARY

Described herein are compositions for the transdermal delivery of amphetamine in the form of a flexible finite system for topical application, comprising a polymer matrix comprising amphetamine or a pharmaceutically acceptable salt or prodrug thereof, wherein the polymer matrix comprises a polymer that is free of vinyl acetate moieties. In some embodiments, the polymer is selected from acrylic polymers that are free of vinyl acetate moieties (such as acrylic polymers made from one or more monomers selected from the group consisting of butyl acrylate, methyl acrylate, methyl methacrylate, acrylic acid, ethyl hexyl acrylate, hydroxy ethyl acrylate and octyl acrylamide), rubber-based polymers (such as polyisobutylene polymers and styrene-isoprene-styrene block copolymers), and mixtures thereof. In some embodiments, the polymer matrix is free of components that include a reactive moiety selected from the group consisting of acetyl moieties, vinyl acetate moieties, acyl halide moieties, carbonate ester moieties, carboxyl moieties, and ester moieties.

In any embodiments, the polymer matrix may further comprise an antioxidant, such as an antioxidant that is free of reactive moieties selected from the group consisting of acetyl moieties, vinyl acetate moieties, acyl halide moieties, carbonate ester moieties, carboxyl moieties, and ester moieties. In some embodiments, the antioxidant is selected from the group consisting of butylated hydroxytoluene (BHT), butylated hydroxyanisole (BHA), and mixtures thereof.

In any embodiments, the polymer matrix may further comprise a component selected from the group consisting of silicone dioxide, hydrogenated hydrocarbon resins, and styrene-isobutylene-styrene block coplymers.

In some embodiments, the composition is stable against the formation of N-acetyl amphetamine. In some embodiments, the composition is stable against the formation of d-amphetamine-related compound B.

In some embodiments, the transdermal drug delivery system includes a backing layer. In some embodiments, the transdermal drug delivery system includes a release liner.

Also provided are methods of manufacturing a composition as described herein comprising forming a blend comprising the polymer and amphetamine or pharmaceutically acceptable salt or prodrug thereof in a solvent that is free of reactive moieties selected from the group consisting of acetyl moieties, vinyl acetate moieties, acyl halide moieties, carbonate ester moieties, carboxyl moieties, and ester moieties. In some embodiments, the solvent is selected from the group consisting of cyclohexane, hexane, pentane, petroleum ether, diethyl ether, tert-butyl methyl ether, tert-butyl alcohol, isopropanol, acetonitrile, ethanol, methanol, isobutyl alcohol, 1-propanol, 2-butanol, isoamyl alcohol, isoamyl alcohol, 1-octanol, p-xylene, m-xylene, toluene, dimethoxyethane, benzene, 1-chlorobutane, tetrahydrofuran, o-xylene, 2-ethoxyethyl ether, n,n-dimethylacetamide, diethylene glycol dimethyl ether, n,n-dimethylformamide, 2-methoxyethanol, pyridine, and mixtures of two or more thereof.

Also provided are methods of manufacturing a composition for the transdermal delivery of amphetamine in the form of a flexible finite system for topical application, comprising forming a blend comprising a polymer and amphetamine or pharmaceutically acceptable salt or prodrug thereof in a solvent that is free of reactive moieties selected from the group consisting of acetyl moieties, vinyl acetate moieties, acyl halide moieties, carbonate ester moieties, carboxyl moieties, and ester moieties. In some embodiments, the solvent is selected from the group consisting of cyclohexane, hexane, pentane, petroleum ether, diethyl ether, tert-butyl methyl ether, tert-butyl alcohol, isopropanol, acetonitrile, ethanol, methanol, isobutyl alcohol, 1-propanol, 2-butanol, isoamyl alcohol, isoamyl alcohol, 1-octanol, p-xylene, m-xylene, toluene, dimethoxyethane, benzene, 1-chlorobutane, tetrahydrofuran, o-xylene, 2-ethoxyethyl ether, n,n-dimethylacetamide, diethylene glycol dimethyl ether, n,n-dimethylformamide, 2-methoxyethanol, pyridine, and mixtures of two or more thereof.

Also provided are compositions for the transdermal delivery of amphetamine made by a method as described herein. Also provided are the compositions as described herein for use in transdermally administering amphetamine to the skin or mucosa of a subject in need thereof, or for achieving central nervous system stimulation or for the treatment of Attention Deficit Disorder (ADD) and/or Attention Deficit/Hyperactivity Disorder (ADHD), and/or for the treatment of narcolepsy. Also provided are the use of amphetamine in the preparation of a medicament in the form of a composition as described herein, for transdermally administering amphetamine to the skin or mucosa of a subject in need thereof, or for achieving central nervous system stimulation or for the treatment of Attention Deficit Disorder (ADD) and/or Attention Deficit/Hyperactivity Disorder (ADHD), and/or for the treatment of narcolepsy.

DETAILED DESCRIPTION

Described herein are transdermal drug delivery compositions comprising amphetamine, methods of making transdermal drug delivery compositions comprising amphetamine and therapeutic methods of using transdermal drug delivery compositions comprising amphetamine. The compositions are provided in a flexible, finite form (e.g., "patch"-type systems) and comprise a polymer matrix that includes amphetamine.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein means that the described composition (e.g., polymer matrix, etc.) comprises less than about 5%, less than about 3%, or less than about 1% by weight, based on the total weight of the composition at issue, of the excluded component(s).

The phrase "free of" as used herein means that the described composition (e.g., polymer matrix, etc.) is formulated without adding the excluded component(s) as an intended component, although trace amounts may be present in other components or as a by-product or contaminant, such that the composition comprises at most only trace amounts of the excluded component(s).

As used herein "subject" denotes any mammal in need of drug therapy, including humans. For example, a subject may be suffering from or at risk of developing a condition that can be treated or prevented with amphetamine (such as ADD, ADHD, or narcolepsy), or may be taking amphetamine for other purposes.

As used herein, the terms "topical" and "topically" mean application to a skin or mucosal surface of a mammal, while the terms "transdermal" and "transdermal" connote passage through the skin or mucosa (including oral, buccal, nasal, rectal and vaginal mucosa), into systemic circulation. Thus, the compositions described herein may be applied topically to a subject to achieve transdermal delivery of amphetamine.

As used herein, the phrases "therapeutically effective amount" and "therapeutic level" mean that drug dosage or plasma concentration in a subject, respectively, that provides the specific pharmacological effect for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As noted above, the compositions described herein are in a "flexible, finite form." As used herein, the phrase "flexible, finite form" means a substantially solid form capable of conforming to a surface with which it comes into contact, and capable of maintaining contact so as to facilitate topical application. Such systems in general are known in the art and commercially available, such as transdermal drug delivery patches.

The compositions comprise a drug-containing polymer matrix that releases amphetamine upon application to the skin (or any other surface noted above). The compositions in flexible, finite form may have a backing layer in addition to the drug-containing polymer matrix layer. In some embodiments, the compositions in flexible, finite form may have a release liner layer in addition to a drug-containing polymer matrix layer and backing layer.

As used herein, "drug-containing polymer matrix" refers to a polymer composition which contains one or more drugs, such as amphetamine, and a polymer, such as a pressure-sensitive adhesive polymer or a bioadhesive polymer. A polymer is an "adhesive" or "bioadhesive" if it has the properties of adhesiveness per se. Other polymers can function as an adhesive or bioadhesive by the addition of tackifiers, plasticizers, crosslinking agents or other excipients. Thus, in some embodiments, the polymer optionally comprises tackifiers, plasticizers, crosslinking agents or other additives known in the art.

As used herein, the term "pressure-sensitive adhesive" refers to a viscoelastic material which adheres instantaneously to most substrates with the application of very slight pressure and remains permanently tacky. As noted above, a polymer is a pressure-sensitive adhesive polymer if it has the properties of a pressure-sensitive adhesive per se. Other polymers may function as a pressure-sensitive adhesive by admixture with tackifiers, plasticizers or other additives. The term pressure-sensitive adhesive also includes mixtures of different polymers.

In some embodiments, the polymer matrix is a pressure-sensitive adhesive at room temperature and exhibits desirable physical properties, such as good adherence to skin, ability to be peeled or otherwise removed without substantial trauma to the skin, retention of tack with aging, etc. In some embodiments, the polymer matrix has a glass transition temperature ($T_g$), measured using a differential scanning calorimeter, of between about −70° C. and 0° C.

In some embodiments, the compositions in flexible, finite form are "monolithic" or "monolayer" systems, such that the drug-containing polymer matrix layer is the only polymeric layer present other than the backing layer and the release liner, if present. In such embodiments, the polymer matrix functions as both the drug carrier and the means of affixing the system to the skin or mucosa.

Amphetamine

Amphetamine (alpha-methylphenethylamine) is a chiral drug. The commercially available oral amphetamine product Adderall® includes several different amphetamine salts, including amphetamine sulfate, amphetamine saccharate, and amphetamine aspartate monohydrate, in an overall ratio of d-amphetamine to l-amphetamine of 3:1. The compositions described herein may be formulated with amphetamine free base or any salt of amphetamine, or any prodrug thereof, or any combinations thereof, and with any isomeric content, and any combinations thereof. In specific embodiments, the compositions comprise d-amphetamine. In further specific embodiments the amphetamine component consists essentially of d-amphetamine (e.g., it contains no more than trace amounts of other amphetamine species). In still further specific embodiments the amphetamine component consists of d-amphetamine. In other specific embodiments, the composition comprises a prodrug of d-amphetamine, such as lisdexamfetamine, in the free base or any salt form, such as lisdexamfetamine dimesylate.

In addition to the salts mentioned above, exemplary suitable pharmaceutically acceptable salts of amphetamine are salts of weak inorganic and organic acids, and quaternary ammonium salts. These include without limitation, salts with acids such as sulfuric, phosphoric, hydrochloric, hydrobromic, hydriodic, sulfamic, citric, lactic, maleic, malic, succinic, tartaric, cinnamic, acetic, benzoic, gluconic, or ascorbic acid, or quaternary ammonium salts with organic esters of sulfuric, hydrohalic, or aromatic sulfonic acids, such as methyl chloride, methyl bromide, ethyl chloride, propyl chloride, butyl chloride, isobutyl chloride, benzylchloride, benzyl bromide, phenethyl bromide, naphthymethyl chloride, dimethyl sulfate, methyl benzenesulfonate, ethyl toluenesulfonate, ethylene chlorohydrin, propylene chlorobydrin, allyl bromide, methylallyl bromide or crotyl bromide esters.

The compositions described herein include a therapeutically effective amount of amphetamine and/or pharmaceutically acceptable salt(s) and/or prodrug(s) thereof. Generally, the amount of amphetamine is from about 1% to about 50%, including from about 5% to about 40%, such as from about 10% to about 20% by weight, based on the total dry weight of the polymer matrix. In specific embodiments, the polymer matrix comprises about 15% by weight amphetamine, based on the total dry weight of the polymer matrix. In other specific embodiments, the polymer matrix comprises about 10% by weight amphetamine, based on the total dry weight of the polymer matrix. In other specific embodiments, the polymer matrix comprises about 20% by weight amphetamine, based on the total dry weight of the polymer matrix.

In accordance with any of the embodiments described herein, the composition may include from about 5 to about 30 mg of amphetamine base or an equivalent amount of a pharmaceutically acceptable salt or prodrug thereof, including about 5, 10, 15, 20, 25, or 30 mg of amphetamine base or equivalent.

Amphetamine may react with certain components that typically are used in the manufacture of transdermal drug delivery compositions, such as components that contain a reactive moiety such as an acetyl moiety, a vinyl acetate moiety, an acyl halide moiety, a carbonate ester moiety, or a carboxyl moiety. Examples of such components include polymers, adhesives, excipients, solvents, or other components that contain an acetyl moiety, a vinyl acetate moiety, an acyl halide moiety, a carbonate ester moiety, a carboxyl moiety, or an ester moiety. For example, amphetamine may react with such a component to form an amphetamine reaction product, such as N-acetyl amphetamine. The formation of an amphetamine reaction product is undesirable from at least two perspectives. First, the formation of an amphetamine reaction product reduces the amount of amphetamine present in the composition, and so may reduce the amount of therapeutically effective amphetamine species, which may impair the efficacy of the compositions. Second, as a general principle, it is desirable to minimize the formation of reaction products and degradants in pharmaceutical products.

The compositions and methods described herein address this problem by formulating and/or manufacturing amphetamine such that the formation of amphetamine reaction products is reduced, minimized, or avoided. Thus, in some embodiments, the polymer matrix comprises a polymer that is free of vinyl acetate moieties. In other embodiments, the polymer matrix is free of components that include reactive moieties, such as acetyl moieties, vinyl acetate moieties, acyl halide moieties, carbonate ester moieties, carboxyl moieties, and ester moieties. Additionally or alternatively, the polymer matrix is made using processing solvents that are free of such reactive moieties.

Polymer Matrix

In accordance with some embodiments, the compositions described herein comprise a polymer matrix that comprises, consists essentially of, or consists of amphetamine and/or pharmaceutically acceptable salt(s) thereof and at least one polymer. In some embodiments, the polymer does not include a vinyl acetate moiety. In other embodiments, the polymer does not include a reactive moiety, such as an acetyl moiety, a vinyl acetate moiety, an acyl halide moiety, a carbonate ester moiety, a carboxyl moiety, or an ester moiety. In this context, the phrase "consists essentially of" means that the polymer matrix is substantially free of components that include a reactive moiety, such as an acetyl moiety, a vinyl acetate moiety, an acyl halide moiety, a carbonate ester moiety, a carboxyl moiety, or an ester moiety, although it may include other components typically used in a transdermal drug delivery composition, such as skin permeation enhancers, tackifiers, plasticizers, crosslinking agents or other excipients known in the art, as long as those other components do not include a reactive moiety, such as an acetyl moiety, a vinyl acetate moiety, an acyl halide moiety, a carbonate ester moiety, a carboxyl moiety, or an ester moiety.

In some embodiments, the polymer matrix comprises an acrylic polymer that is free of vinyl acetate groups, such as a pressure-sensitive adhesive acrylic polymer that is free of vinyl acetate groups. Examples of such acrylic polymers include acrylic polymers made from butyl acrylate monomers, methyl acrylate monomers, methyl methacrylate monomers, acrylic acid monomers, ethyl hexyl acrylate monomers, and/or hydroxy ethyl acrylate monomers, as well as methacrylic acid, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, and tridecyl methacrylate. In specific embodiments, the acrylic polymer is made from one or more of ethyl hexyl acrylate, methyl acrylate, methyl methacrylate, butyl acrylate, and octyl acrylamide monomers. In further specific embodiments, the acrylic polymer is made from each of ethyl hexyl acrylate, methyl acrylate, butyl acrylate, and octyl acrylamide monomers. In further specific embodiments, the polymer matrix includes two or more acrylic polymer that each are made from one or more of ethyl hexyl acrylate, methyl acrylate, butyl acrylate, and octyl acrylamide monomers. Suitable acrylic polymers can be obtained commercially or by polymerizing or copolymerizing suitable monomers such as acrylic monomers and other polymerizable monomers, such as those set forth above.

Acrylate monomers which can be used include acrylic acid, methacrylic acid, methyl methacrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, and octyl acrylamide. In specific embodiments, the non acid-functional acrylic polymer includes methacrylate monomers and 2-ethylhexyl acrylate monomers. In other specific embodiments the non acid-functional acrylic polymer includes methacrylate monomers, 2-ethylhexyl acrylate monomers, and amide-group containing monomers such as octylacrylamide.

Suitable acrylic polymers which are commercially available include those sold by Henkel North America under the Duro-Tak® brand name such as Durotak® 87-2353, 73-9257, 73-9259, 73-9261, 87-2097, 87-2510,87-4098, 87-9301A, 87-900A, 87-901A, 87-9082, 87-9085, 87-9088, and by Cytec Industries Inc. under the Gelva® GMS brand name, such as Gelva® GMS 3071, GMS 3067, GMS 3087, and GMS 3235. Other suitable acrylic polymers are known in the art. See, e.g., the non acid-functional acrylic polymers described in Satas, "Acrylic Adhesives, HANDBOOK OF PRESSURE-SENSITIVE ADHESIVE TECHNOLOGY, 2nd ed., pp. 396-456 (D. Satas, ed.), Van Nostrand Reinhold, N. Y. (1989); "Acrylic and Methacrylic Ester Polymers," POLYMER SCIENCE AND ENGINEERING, Vol. 1, 2nd ed., pp 234-268, John Wiley & Sons, (1984).

In some embodiments, the polymer matrix additionally or alternatively comprises a rubber-based polymer, such as a rubber-based adhesive polymer. Examples of suitable rubber-based polymers include polyisobutylene polymers and styrene-isoprene-styrene block copolymers.

Polyisobutylene polymers suitable for use in a polymer matrix of transdermal drug delivery compositions are known, and include those sold by BASF under the Oppanol® brand, such as Oppanol® B11. In some embodiments, the polymer matrix comprises two or more polyisobutylene polymers of different molecular weights. In accordance with these embodiments, the relative amounts of polyisobutylene polymers can be selected and tailored to produce a product with satisfactory physical and pharmacokinetic properties.

Styrene-isoprene-styrene block copolymers suitable for use in a polymer matrix of transdermal drug delivery compositions are known, and include those sold by Kraton under the Kraton® brand, such as Kraton® D111 KT.

In some embodiments, the polymer matrix is substantially free of silicone polymers. In some embodiments, the polymer matrix is free of silicone polymers. By "free of silicone polymers" is meant that the composition is formulated without silicone polymers, such that at most only trace amounts are present as impurities or contaminants.

When the polymer matrix comprises more than one polymer, each polymer can be included in any amount. The relative amounts of each polymer can be selected and tailored to achieve desired physical properties (e.g., strength, tackiness, peel strength, etc.), desired drug solubility/drug loading, and/or desired pharmacokinetic properties (e.g., onset and duration of drug delivery and drug delivery profile, etc.).

Other Components

As noted above, the polymer matrix of the compositions described herein optionally may further comprise other components typically used in a transdermal drug delivery composition, such as tackifiers, plasticizers, crosslinking agents or other excipients known in the art. In some embodiments, any such components that are present do not include a reactive moiety, such as an acetyl moiety, a vinyl acetate moiety, an acyl halide moiety, a carbonate ester moiety, a carboxyl moiety, or an ester moiety.

Amphetamine contains a primary amine group which is subject to oxidization in the presence of an oxidizing agent such as oxygen. This can result in the formation of undesired compounds during processing and/or storage, such as phenyl acetone. The oxidation of amphetamine can be reduced, minimized or prevented by including an antioxidant in the polymer matrix. In some embodiments, the antioxidant is butylhydroxytoluene (BHT) and/or butylhydroxyanisole (BHA). In other embodiments, the antioxidant is, additionally or alternatively, tertiary-butyihydroquinone (TBHQ). In other embodiments, the antioxidant is, additionally or alternatively, alpha tocopherol, ascorbic-acid, ascorbyl palmitate, propyl gallate, fumaric acid, malic acid, sodium ascorbate, sodium metabisulfite, and the like. In specific embodiments, the antioxidant does not include a reactive moiety, such as such as an acetyl moiety, a vinyl acetate moiety, an acyl halide moiety, a carbonate ester moiety, a carboxyl moiety, or an ester moiety. In specific embodiments, the antioxidant (or combinations thereof) are used in a total amount of from about 0.01 to about 5.0% by weight, including from about 0.1 to about 1.0% by weight, such as about 0.1% by weight, about 0.25% by weight, and about 0.5% by weight, based on the dry weight of the polymer matrix.

The polymer matrix may further comprise various tackifying agents, thickeners, fillers, and other additives or components known for use in transdermal drug delivery systems. These optional components include tackifying agents such as aliphatic hydrocarbons, mixed aliphatic and aromatic hydrocarbons, aromatic hydrocarbons, substituted aromatic hydrocarbons, hydrogenated esters, hydrogenated hydrocarbon resins, styrene-isobutylene-styrene block copolymers, polyterpenes, silicone fluid, mineral oil and hydrogenated wood rosins; binders, such as lecithin which "bind" the other ingredients; rheological agents (thickeners) containing silicone, such as fumed silica, reagent grade sand, precipitated silica, amorphous silica, colloidal silicon dioxide, fused silica, silica gel, quartz and particulate siliceous materials commercially available as Syloid®, Cabosil®, Aerosil®, and Whitelite®, such as for enhancing the uniform consistency or continuous phase of the composition or coating. Other additives and excipients include diluents, stabilizers, fillers, clays, buffering agents, biocides, humectants, anti-irritants, antioxidants, preservatives, plasticizing agents, cross-linking agents, flavoring agents, colorants, pigments and the like. Such substances can be present in any amount sufficient to impart the desired properties to the composition. As noted above, in some embodiments, any such components that are present do not include a reactive moiety, such as an acetyl moiety, a vinyl acetate moiety, an acyl halide moiety, a carbonate ester moiety, a carboxyl moiety.

Such additives or excipients are typically used in amounts totaling up to 50%, including from about 0.1% to about 30%, by weight based on the dry weight of the polymer matrix. As noted above, in some embodiments, any such components that are present do not include a reactive moiety, such as an acetyl moiety, a vinyl acetate moiety, an acyl halide moiety, a carbonate ester moiety, a carboxyl moiety.

In specific embodiments, the polymer matrix includes silicone dioxide, such as colloidal silicone dioxide, in an amount of about 5.0% to about 30%, including about 15% or about 20%, by weight based on the dry weight of the polymer matrix.

In specific embodiments, the polymer matrix includes a hydrogenated hydrocarbon resin, in an amount of about 5.0% to about 50%, including about 35% by weight based on the dry weight of the polymer matrix.

In specific embodiments, the polymer matrix includes a styrene-isobutylene-styrene block copolymer, in an amount of about 5.0% to about 50%, including about 30% by weight based on the dry weight of the polymer matrix.

Amphetamine base does not generally require a penetration enhancer. Thus, in some embodiments, the polymer matrix is substantially free of penetration enhancers. In some embodiments, the polymer matrix is free of penetration enhancers. By "free of penetration enhancers" is meant that the composition is formulated without penetration enhancers, such that at most only trace amounts are present as impurities or contaminants.

Transdermal Drug Delivery Systems

In embodiments where the polymer matrix comprises a pressure-sensitive adhesive or bioadhesive, the polymer matrix can serve as an adhesive portion of the transdermal drug delivery system (e.g., a reservoir device), or can serve as one or more layers of a multi-layer system. Alternatively, a polymer matrix comprising a pressure-sensitive adhesive or bioadhesive with drug dissolved or dispersed therein can constitute a monolithic transdermal drug delivery system. In embodiments where the polymer matrix does not comprise an adhesive, but instead, for example, comprises a polymeric drug reservoir, it can be used in combination with one or more adhesive layers, or with a surrounding adhesive portion, as is well known to those skilled in the art.

In some embodiments, a transdermal drug delivery system consists essentially of the polymer matrix layer. By "consists essentially of the polymer matrix layer" means that the system does not contain any other layers that affect drug delivery, such as an additional rate-controlling polymer layer, rate-controlling membrane, or drug reservoir layer. It will be understood, however, that the system that consists essentially of the polymer matrix layer may comprise a backing layer and/or release liner.

The transdermal drug delivery system may be of any shape or size suitable for transdermal application.

Backing Layer

The transdermal drug delivery system also may include a drug impermeable backing layer or film. (By "impermeable" to the drug is meant that no substantial amount of drug loss through the backing layer is observed.) In some embodiments, the backing layer is adjacent one face of the polymer matrix layer. When present, the backing layer protects the polymer matrix layer (and any other layers present) from the environment and prevents loss of the drug and/or release of other components to the environment during use. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak™ 1012, 9732, 1109, 9680, 9734, 9700, 9719 or 9722 backing material (a polyester film with an ethylene vinyl acetate copolymer heat seal layer) is useful in the transdermal drug delivery systems described herein.

Release Liner

The transdermal drug delivery system also may include a release liner, typically located adjacent the opposite face of the system as compared to the backing layer. When present, the release liner is removed from the system prior to use to expose the polymer matrix layer and/or an adhesive layer prior to topical application. Materials suitable for use as release liners are well-known known in the art and include the commercially available products of Dow Corning Corporation designated Bio-Release® liner and Syl-off® 7610 (both silicone-based) and 3M's 1020, 1022, 9744, 9748 and 9749 Scotchpak™ (fluoropolymer coated polyester films).

The transdermal drug delivery system may be packaged or provided in a package, such as a pouchstock material used in the prior art for transdermal drug delivery systems. For example, DuPont's Surlyn® can be used in a pouchstock material.

As noted above, a "monolithic" transdermal drug delivery system may include a backing layer and/or release liner, and may be provided in a package.

Methods Of Manufacturing Transdermal Drug Delivery Compositions And Systems

The polymer matrices described herein may be prepared by methods known in the art. For example, the polymer matrix material can be applied to a backing layer and release liner by methods known in the art, and formed into sizes and shapes suitable for use. For example, after the polymer matrix is formed, it may be brought into contact with a support layer, such a releaser liner layer or backing layer, in any manner known to those of skill in the art. Such techniques include calender coating, hot melt coating, solution coating, etc.

For example, a polymer matrix can be prepared by blending the components of the polymer matrix, applying the matrix material to a support layer such as a backing layer or release liner, and removing any remaining solvents. The therapeutically active agents can be added at any stage. In one embodiment, all polymer matrix components, including the therapeutically active agents, are blended together. In another embodiment, the polymer matrix components other than the therapeutically active agents are blended together, and then the therapeutically active agents are dissolved or dispersed therein. The order of steps, amount of ingredients, and the amount and time of agitation or mixing can be determined and optimized by the skilled practitioner. An exemplary general method is as follows:

Appropriate amounts of polymer(s), enhancer(s), and organic solvent(s) are combined and thoroughly mixed together in a vessel.

The formulation is transferred to a coating operation where it is coated onto a protective release liner at a controlled specified thickness.

The coated product is passed through an oven in order to drive off all volatile processing solvents.

The dried product on the release liner is then joined to the backing material and wound into rolls for storage.

Appropriate size and shape "systems" are die-cut from the roll material and then pouched.

Other manufacturing methods are known in the art that are suitable for making the systems described herein.

Also provided are methods of manufacturing transdermal drug delivery compositions comprising amphetamine using processing solvents that are chosen so as to reduce, minimize or avoid the use of solvents that include a reactive moiety, such as an acetyl moiety, a vinyl acetate moiety, an acyl halide moiety, a carbonate ester moiety, a carboxyl moiety, or an ester moiety. For example, in some embodiments, a transdermal drug delivery composition is made without the use of solvents that include a reactive moiety, such as an acetyl moiety, a vinyl acetate moiety, an acyl halide moiety, a carbonate ester moiety, a carboxyl moiety, or an ester moiety. For example, in some embodiments, a transdermal drug delivery composition is made without the use of ethyl acetate, which has an ester moiety, which may result in the formation of acetyl amphetamine.

Suitable processing solvents that do not include a reactive moiety include cyclohexane, hexane, pentane, petroleum ether, diethyl ether, tert-butyl methyl ether, tert-butyl alcohol, isopropanol, acetonitrile, ethanol, methanol, isobutyl alcohol, 1-propanol, 2-butanol, isoamyl alcohol, isoamyl alcohol, 1-octanol, p-xylene, m-xylene, toluene, dimethoxyethane, benzene, 1-chlorobutane, tetrahydrofuran, o-xylene, 2-ethoxyethyl ether, n,n-dimethylacetamide, diethylene glycol dimethyl ether, n,n-dimethylformamide, 2-methoxyethanol, pyridine, and the like. In specific embodiments, one or more of these solvents is used to prepare a polymer matrix. For example, all polymer components, amphetamine, and any optional components may be formulated in one or more of these solvents, or other solvents that do not include a reactive moiety, and then the resulting formulation may be applied to a support layer (e.g., a backing layer or release liner) and further processed as outlined above.

Therapeutic Methods

The compositions described herein are useful in methods for the transdermal delivery of amphetamine, including in methods for treating Attention Deficit Disorder (ADD) and/or Attention Deficit/Hyperactivity Disorder (ADHD), and/or narcolespy. In such embodiments, a composition comprising a therapeutically effective amount of amphetamine as described herein is topically applied to a subject in need thereof.

In some embodiments, the compositions achieve transdermal delivery of amphetamine over a period of time of about 8 to 10 hours, including a period of time of about 9 hours, although the composition may remain on the application site for a longer period of time.

The compositions described herein achieve a transdermal flux of amphetamine (and/or one or more pharmaceutically acceptable salt(s) thereof) that is sufficient to have a therapeutic effect. As used herein, "flux" (also called "permeation rate") is defined as the absorption of a drug through skin or mucosal tissue, and is described by Fick's first law of diffusion:

$$J = -D(dCm/dx)$$

where J is the flux in $g/cm^2/sec$, D is the diffusion coefficient of the drug through the skin or mucosa in $cm^2/sec$ and dCm/dx is the concentration gradient of the drug across the skin or mucosa.

The following specific examples are included as illustrative of the compositions described herein. These example are in no way intended to limit the scope of the invention. Other aspects of the invention will be apparent to those skilled in the art to which the invention pertains.

EXAMPLES 1 AND 2

Polymer matrix compositions were prepared as set forth below, using either cyclohexane or ethyl acetate as the processing solvent. The composition formulated using ethyl acetate as the processing solvent exhibited the formation of N-acetyl amphetamine.

| Ingredient | Example 1 | Example 2 |
|---|---|---|
| Amphetamine Base | 15% | 15% |
| Acrylic Polymer (monomers: ethyl hexyl acrylate; methyl acrylate, butyl acrylate; octyl acrylamide) | 85% | 85% |
| Processing Solvent | Cyclohexane | Ethyl Acetate |
| N-Acetyl-Amphetamine | 0.0% | 0.3% |

EXAMPLES 3-5

Polymer matrix compositions were prepared as set forth below, using different polymer components. Compositions formulated with polymer comprising vinyl acetate moieties exhibited greater formation of N-acetyl amphetamine.

| Ingredient | Example 3 | Example 4 | Example 5 |
|---|---|---|---|
| Amphetamine Base | 15% | 15% | 15% |
| Acrylic Polymer (monomers: ethyl hexyl acrylate; methyl acrylate; butyl acrylate; octyl acrylamide) | 85% | | |
| Acrylic Polymer (monomers: ethyl hexyl acrylate; methyl acrylate) | | 85% | |
| Acrylic Polymer (monomers: ethyl hexyl acrylate; vinyl acetate) | | | 85% |
| N-Acetyl Amphetamine | 0.0% | 0.3% | 13.2% |

EXAMPLES 6-8

Polymer matrix compositions were prepared as set forth below, using different excipients components. Compositions formulated with an excipients comprising a vinyl acetate moiety exhibited the formation of N-acetyl amphetamine.

| Ingredient | Example 6 | Example 7 | Example 8 |
|---|---|---|---|
| Amphetamine Base | 15% | 15% | 15% |
| Acrylic Polymer (monomers: ethyl hexyl acrylate; methyl acrylate; butyl acrylate; octyl acrylamide) | 85% | 65% | 55% |
| Excipient that contains silicone dioxide | | 20% | |
| Excipient that contains copolymer of 72% ethylene and 28% vinyl acetate | | | 30% |
| N Acetyl Amphetamine | 0.0% | 0.0% | 0.4% |

EXAMPLES 9-12

Polymer matrix compositions were prepared as set forth below, with and without BHT and/or BHA. Compositions formulated without BHT and BHA exhibited greater formation of d-amphetamine related compound B.

| Ingredient | Example 9 | Example 10 | Example 11 | Example 12 |
|---|---|---|---|---|
| Amphetamine | 15% | 15% | 15% | 15% |
| Acrylic Polymer (monomers: ethyl hexyl acrylate; methyl acrylate; butyl acrylate; octyl acrylamide) | 85% | 65% | 55% | 55% |
| Excipient that contains silicone dioxide | 20% | 20% | 20% | 20% |
| Butylated Hydroxytoluene (BHT) | 0.5% | 0.0% | 0.25% | 0.0% |
| Butylated Hydroxyanisole (BHA) | 0.0% | 0.5% | 0.25% | 0.0% |
| d-Amphetamine-Related Compound B | 0.1% | 0.1% | 0.1% | 0.5% |

EXAMPLES 13-15

Polymer matrix compositions were prepared as set forth below, with either a hydrogenated hydrocarbon resin (HHR) or styrene-isobutylene-styrene (SIBS). Compositions formulated with BHT and HHR or SIBS exhibited less formation of d-amphetamine related compound B than compositions with adhesive only.

| Ingredient | Example 13 | Example 14 | Example 15 |
|---|---|---|---|
| Amphetamine | 15% | 15% | 15% |
| Acrylic Polymer (monomers: ethyl hexyl acrylate, methyl acrylate, butyl acrylate and octyl acrylamide | 50% | 54% | 85% |
| Excipient contains hydrogenated hydrocarbon resin (HHR) | 34% | — | — |
| Excipient contains styrene-isobutylene-styrene (SIBS) | — | 30% | — |
| Butylated Hydroxytoluene (BHT) | 1% | 1% | — |
| d-Amphetamine-Related Compound B | 0.0% | 0.1% | 1.7% |

What is claimed is:

1. A composition for the transdermal delivery of amphetamine through skin in the form of a monolithic, flexible, finite transdermal drug delivery system for topical application to skin, consisting of a drug-impermeable backing layer, a single polymer layer and, optionally, a release liner,
    wherein the single polymer layer comprises amphetamine or a pharmaceutically acceptable salt or prodrug thereof in a polymer matrix that comprises an antioxidant and a polymer that is free of vinyl acetate moieties and is selected from:
    acrylic polymers made from one or more monomers selected from butyl acrylate, methyl acrylate, methyl methacrylate, acrylic acid, ethyl hexyl acrylate, hydroxy ethyl acrylate, and octyl acrylamide, and
    rubber-based polymers selected from polyisobutylene polymers and styrene-isoprene-styrene block copolymers,
    and mixtures thereof.

2. The composition of claim 1, wherein the polymer comprises an acrylic polymer made from one or more monomers selected from butyl acrylate, methyl acrylate, methyl methacrylate, acrylic acid, ethyl hexyl acrylate, and hydroxy ethyl acrylate.

3. The composition of claim 1, wherein the polymer comprises a rubber-based polymer selected from polyisobutylene polymers and styrene-isoprene-styrene block copolymers.

4. The composition of claim 1, wherein the polymer matrix is free of components that include a reactive moiety selected from acetyl moieties, vinyl acetate moieties, acyl halide moieties, carbonate ester moieties, carboxyl moieties, and ester moieties.

5. The composition of claim 1, wherein the antioxidant is free of reactive moieties selected from acetyl moieties, vinyl acetate moieties, acyl halide moieties, carbonate ester moieties, carboxyl moieties, and ester moieties.

6. The composition of claim 1, wherein the antioxidant is selected from butylated hydroxytoluene (BHT), butylated hydroxyanisole (BHA), and mixtures thereof.

7. The composition of claim 1, wherein the polymer matrix further comprises a component selected from silicon dioxide, hydrogenated hydrocarbon resins, and styrene-isobutylene-styrene block.

8. The composition of claim 1, wherein the composition is stable against the formation of N-acetyl amphetamine.

9. The composition of claim 1, wherein the composition is stable against the formation of phenyl acetone (d-amphetamine-related compound B).

10. The composition according to claim 1, wherein the release liner is present.

11. The composition of claim 1, wherein the polymer matrix comprises at least 50% by weight acrylic polymer free of vinyl acetate moieties.

12. The composition of claim 1, wherein the polymer comprises an acrylic polymer made from ethyl hexyl acrylate, methyl acrylate, methyl methacrylate, butyl acrylate, and octyl acrylamide monomers.

13. The composition of claim 12, wherein the antioxidant is selected from butylated hydroxytoluene (BHT), butylated hydroxyanisole (BHA), and mixtures thereof.

14. A method of transdermally administering amphetamine through skin, comprising topically applying a composition according to claim 1 to the skin of a subject in need thereof, after removing the release liner, if present.

* * * * *